United States Patent [19]

Stroever et al.

[11] Patent Number: 5,728,159
[45] Date of Patent: Mar. 17, 1998

[54] SERRATED BONE GRAFT

[75] Inventors: Bruce W. Stroever, Long Valley; Thomas P. Rainey, Florham, both of N.J.

[73] Assignee: Musculoskeletal Transplant Foundation, Holmdel, N.J.

[21] Appl. No.: 778,266

[22] Filed: Jan. 2, 1997

[51] Int. Cl.[6] .................................................. A61F 2/28
[52] U.S. Cl. .................................................. 623/16; 623/17
[58] Field of Search .................................. 623/16, 18, 17; 606/60, 61

[56] References Cited

U.S. PATENT DOCUMENTS

| | | |
|---|---|---|
| 2,677,369 | 5/1954 | Knowles ................................. 623/17 |
| 4,834,757 | 5/1989 | Brantigan . |
| 4,950,296 | 8/1990 | McIntyre ................................. 623/16 |
| 5,112,354 | 5/1992 | Sires . |
| 5,192,327 | 3/1993 | Brantigan ................................. 623/17 |
| 5,320,644 | 6/1994 | Baumgartner . |
| 5,439,684 | 8/1995 | Prewett et al. . |
| 5,593,409 | 1/1997 | Michelson . |
| 5,609,636 | 3/1997 | Kohrs et al. . |

*Primary Examiner*—Debra S. Brittingham
*Attorney, Agent, or Firm*—Rothwell, Figg, Ernst & Kurz, P.C.

[57] ABSTRACT

A serrated bone graft section for graft in a patient includes a body portion cut from elongate cortical bone, the body portion having a sidewall portion, the body portion having substantially planar end faces at opposite ends of said body portion, each of the end faces having a plurality of grooves cut therein so as to form serrations in each of the end faces.

14 Claims, 3 Drawing Sheets

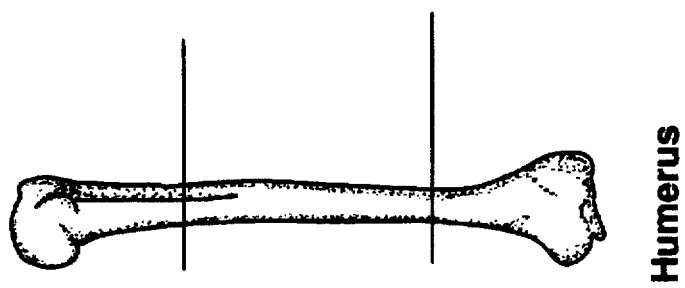
FIG.8C  Humerus
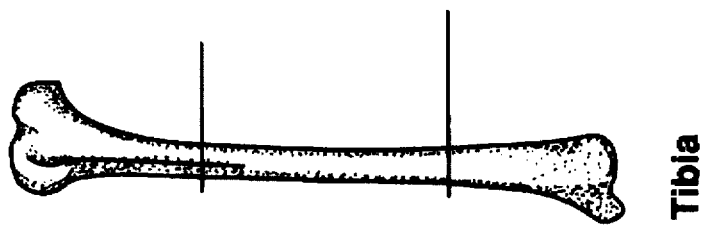
FIG.8B  Tibia
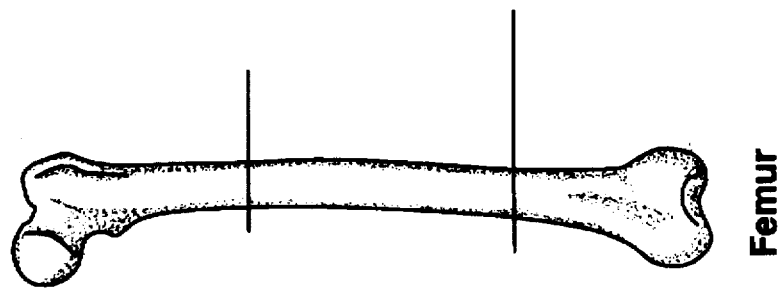
FIG.8A  Femur

SERRATED BONE GRAFT

BACKGROUND OF THE INVENTION

1. Field of the Invention

The present invention relates to the field of bone grafts.

2. Description of the Background Art

U.S. Pat. No. 4,950,296 discloses combined cortical and cancellous bone grafting units and methods of making same. The units disclosed therein have an elongated cylindrical cortical body member with flat, planar ends and a cylindrical cavity extending transverse to the axis of the body in which is packed a cancellous bone plug.

There remains a need in the art for improved bone graft configurations.

SUMMARY OF THE INVENTION

According to the present invention, a bone graft section for graft in a patient comprises a body portion cut from elongate cortical bone, the body portion having a sidewall portion, the body portion having substantially planar end faces at opposite ends of the body portion, each of the end faces having a plurality of grooves cut therein so as to form serrations in each of the end faces.

BRIEF DESCRIPTION OF THE DRAWINGS

FIGS. 8A, 8B and 8C are respective perspective views of a femur, tibia and humerus, from which serrated bone grafts in accordance with the present invention can be formed.

DETAILED DESCRIPTION OF THE PREFERRED EMBODIMENTS

Figure 1:
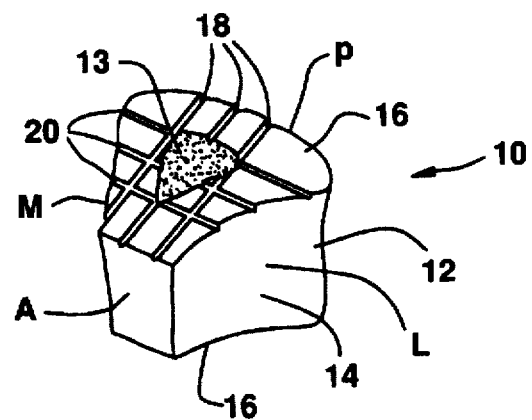
FIG. 1 is a perspective view of a serrated fibular cross-section bone graft in accordance with one embodiment of the present invention.

Serrated bone graft sections in accordance with the present invention can be cut from whole diaphyseal bone at about mid-shaft approximately 50 mm from the proximal and distal ends of the bone. Exemplary lengths of serrated bone graft sections in accordance with the present invention range from about 8 mm to about 80 mm, with exemplary diameters ranging from about 10 mm to about 27 mm.

FIGS. 1-7 show various embodiments of the invention, where corresponding parts are labeled with the same reference number. Each of these serrated bone graft sections 10 shown in FIGS. 1-7 includes a body portion 12 cut from elongate cortical bone, the body portion 12 having a sidewall portion 14. The body portion 12 further has substantially planar end faces 16 (one shown in each of FIGS. 1-7) at opposite ends of body portion 12. Each of the end faces 16 includes a plurality of grooves 18, 20 cut therein, so as to form serrations in each of end faces 16.

In preferred embodiments, at least about three grooves 18 are cut parallel in end faces 16 in the anterior/posterior (A/P) direction of section 10, and at least about three grooves 20 are cut parallel in end faces 16 in the medial/lateral (M/L) direction of section 10. In the embodiment shown, grooves 18, 20 are cut so as to cross on end faces 16. In particularly preferred embodiments, grooves 18, 20 are cut perpendicular to each other.

In exemplary embodiments, grooves 18, 20 are cut within the range of from about 0.1 mm to about 2 mm in both depth and width. In particularly preferred embodiments, grooves 18, 20 are approximately 1 mm deep and approximately 1 mm wide.

The serrated fibular cross-section bone grafts shown in FIG. 1 can have exemplary diameters of about 10-14 mm and about 15-18 mm, with exemplary length of 8 mm, 10 mm, 12 mm and 14 mm. Additionally, elongate shaft embodiments can have equivalent diameters, but exemplary lengths of 20 mm, 30 mm, 40 mm, 50 mm, 60 mm, 70 mm and 80 mm. In particularly preferred embodiments, the cortical wall thickness is greater than or equal to about 2 mm, and the spine of the bone is removed for uniformity in wall thickness. The serrated fibular cross-section bone graft has end faces 16 which are substantially parallel to each other.

Figure 2:
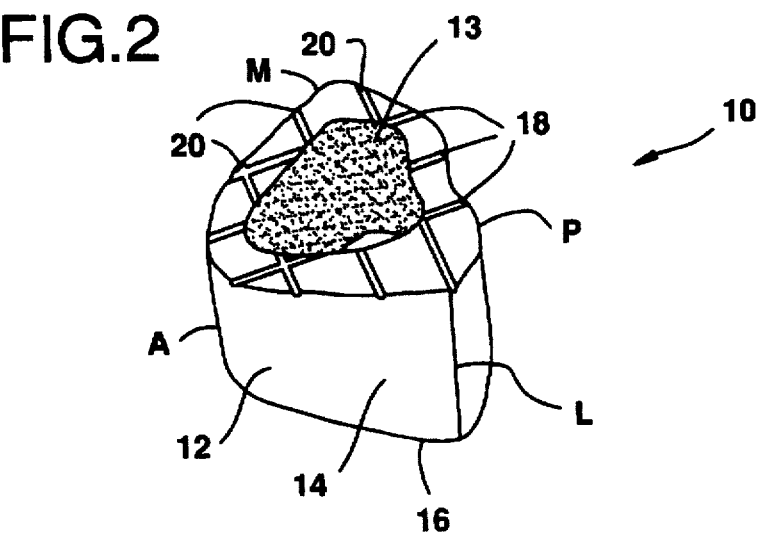
FIG. 2 is a perspective view of a serrated humeral cross-section bone graft in accordance with another embodiment of the present invention.

The serrated humeral cross-section bone grafts shown in FIG. 2 can have exemplary diameters within the range of about 19-22 mm, and exemplary lengths of 8 mm, 10 mm, 12 mm and 14 mm. Elongate shaft embodiments can have equivalent diameters as in the serrated fibular cross-section bone grafts, which may be within the exemplary range of about 20-80 mm. The serrated humeral cross-section bone graft has end faces 16 which are substantially parallel to each other. In preferred embodiments, the cortical wall thickness is greater than or equal to about 3 mm, and the spine is removed from the bone for greater wall thickness uniformity.

Figure 3:
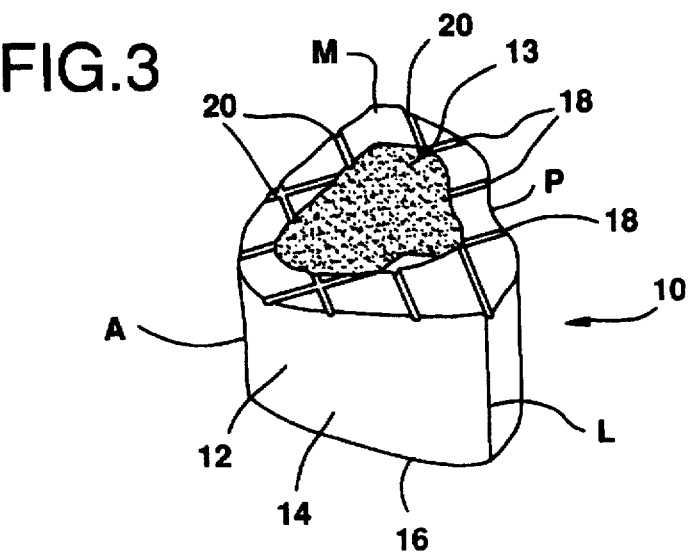
FIG. 3 is a perspective view of a serrated tibial cross-section bone graft in accordance with another embodiment of the present invention.
Figure 4:
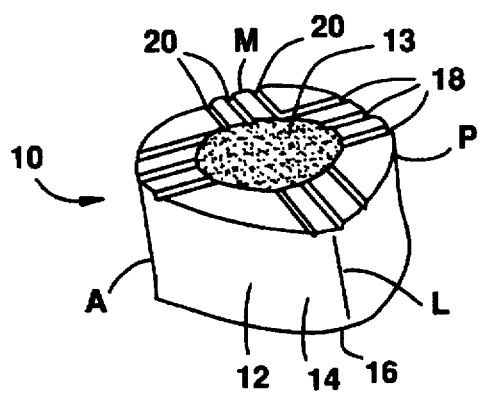
FIG. 4 is a perspective view of a serrated femoral cross-section bone graft in accordance with another embodiment of the present invention.

The serrated tibial cross-section and serrated femoral cross-section bone grafts shown respectively in FIGS. 3 and 4 can have exemplary diameters within the range of 23-27 mm, and exemplary lengths of about 10 mm, 12 mm, 14 mm and 16 mm. Each of the serrated tibial cross-section and serrated femoral cross-section bone grafts has parallel end faces. Shaft embodiments of these bone grafts have lengths corresponding to those of the serrated fibular shaft embodiments, within the exemplary range of 20-80 mm. In preferred embodiments, the cortical wall thickness in the tibial cross-section bone graft is greater than or equal to about 4 mm, while in the femoral cross-section bone graft, the cortical wall thickness is greater than or equal to 5 mm, and in both cases, the spine is removed from the bone for greater wall thickness uniformity.

Figure 5:
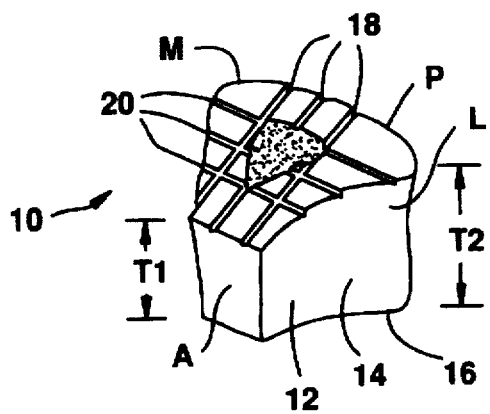
FIG. 5 is a perspective view of a serrated fibular wedge bone graft in accordance with another embodiment of the present invention.
Figure 6:
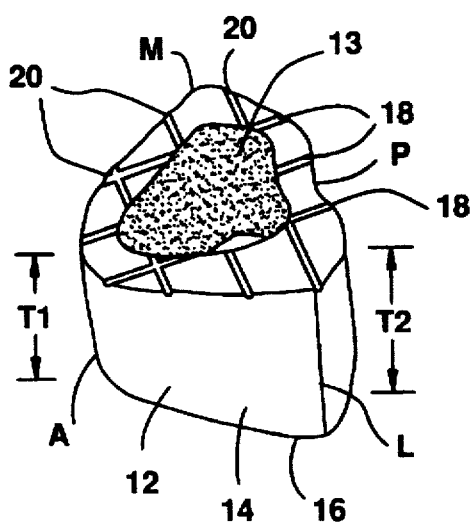
FIG. 6 is a perspective view of a serrated humeral wedge bone graft in accordance with another embodiment of the present invention.
Figure 7:
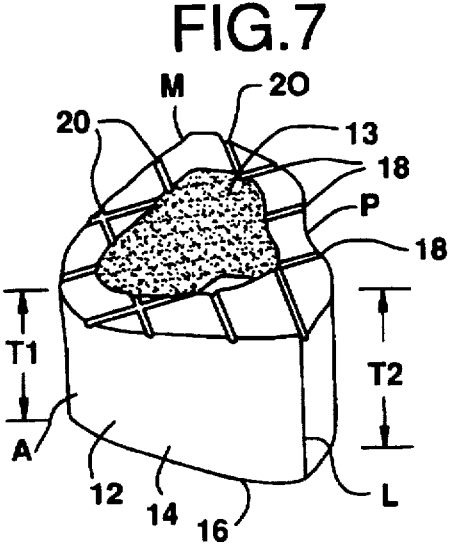
FIG. 7 is a perspective view of a serrated tibial wedge bone graft in accordance with another embodiment of the present invention.

The serrated bone grafts shown in FIGS. 5-7 are wedges, i.e., the substantially planar end faces 16 are angled with respect to each other, with the angle between the planar end faces being defined by the T1 and T2 measurements shown in FIGS. 5-7.

The serrated fibular wedge bone graft shown in FIG. 5 can have exemplary diameters within the range of about 15-18 mm, and exemplary respective T1/T2 lengths of 5 mm/8 mm, 7 mm/10 mm, 9 mm/12 mm and 11 mm/14 mm. In preferred embodiments, the cortical wall thickness is greater than or equal to about 2 mm, and the spine is removed from the bone for greater wall thickness uniformity.

Serrated humeral wedge bone grafts as shown in FIG. 6 can have exemplary width dimensions within the range of about 19–22 mm, and exemplary T1/T2 length dimensions of about 11 mm/14 mm, 13 mm/16 mm, 15 mm/18 mm and 17 mm/20 mm. In preferred embodiments, the cortical wall thickness is greater than or equal to about 3 mm, and the spine is removed from the bone for greater wall thickness uniformity.

Serrated tibial wedge bone grafts as shown in FIG. 7 can have exemplary width dimensions with the range of about 23–27 mm, and exemplary T1/T2 length dimensions of about 11 mm/14 mm, 13 mm/16 mm, 15 mm/18 mm and 17 mm/20 mm. In preferred embodiments, the cortical wall thickness is greater than or equal to about 4 mm, and the spine is removed from the bone for greater wall thickness uniformity.

In preferred embodiments, the cortical bone from which the serrated bone graft sections in accordance with the present invention are cut are light grey, cream or white in color, and substantially free of blood products and lipids. The medullary canal and cortical plates also are substantially free of blood products and lipids.

The body portion 12 of each serrated bone graft section 10 has a transverse cavity 13 (intermedullary canal) extending through body portion 12 between opposite end faces 16. If desired, the transverse cavity 13 can receive allograft (e.g., non-cancellous allograft) or a patient's autogenous tissue, such as the patient's own bone material and blood.

FIGS. 8A, 8B and 8C respectively show a femur, humerus and tibia, from which serrated bone graft sections in accordance with the present invention can be cut.

The serrated end faces of bone graft sections in accordance with the present invention increase the interbody stability of the grafts during use.

The bone material from which a graft in accordance with the present invention is formed preferably is aseptic and substantially pure bone mineral, i.e., is substantially protein-free, substantially lipid-free and substantially blood-free. Advantageously, the material from which a graft in accordance with the present invention is prepared is processed aseptically in a level 10 clean room utilizing a system that includes one or more ultrasonic baths, ethanol treatment, antibiotic soap, and blood/lipid removal steps, all of which are known in the art.

Because many modifications, variations and changes in detail may be made to the described embodiments, it is intended that all matter in the foregoing description and shown in the accompanying drawings be interpreted as illustrative and not in a limiting sense.

We claim:

1. A serrated bone graft section for graft in a patient, comprising a body portion cut from elongate cortical bone, the body portion having a sidewall portion, the body portion having substantially planar end faces at opposite ends of said body portion, each of the end faces having a plurality of grooves cut therein so as to form cross-cut serrations in each of the end faces, wherein a substantial portion of each end face planar surface area.

2. The section of claim 1, wherein said planar end faces are parallel with respect to each other.

3. The section of claim 2, wherein said plurality of grooves includes a first set of substantially parallel grooves in each end face.

4. The section of claim 3, further including a second set of substantially parallel grooves in each of the end faces which crosses said first set of substantially parallel grooves to form said cross-cut serrations.

5. The section of claim 4, wherein the first and second sets of substantially parallel grooves are substantially perpendicular to each other.

6. The section of claim 5, wherein the first and second sets of substantially parallel grooves each include at least about three grooves.

7. The section of claim 6, wherein said body portion has a length of from about 8 mm to about 80 mm, and wherein said body portion has a diameter of from about 10 mm to about 27 mm.

8. A serrated bone graft section for graft in a patient, comprising a body portion cut from elongate cortical bone, the body portion having a sidewall portion, the body portion having substantially planar end faces at opposite ends of said body portion, each of the end faces having a plurality of grooves cut therein so as to form cross-cut serrations in each of the end faces, wherein a substantial portion of each end face is planar surface area wherein said substantially planar end faces are not parallel, and are angled with respect to each other.

9. The section of claim 8, wherein said plurality of grooves includes a first set of substantially parallel grooves in each end face.

10. The section of claim 9, further including a second set of substantially parallel grooves in each of the end faces which crosses said first set of substantially parallel grooves to form said cross-cut serrations.

11. The section of claim 10, wherein the first and second sets of substantially parallel grooves are substantially perpendicular to each other.

12. The section of claim 11, wherein the first and second sets of substantially parallel grooves each include at least about three grooves.

13. The section of claim 12, having an anterior length dimension (T1) of from about 5 mm to about 17 mm, and a posterior length dimension (T2) of from about 8 mm to about 20 mm.

14. The section of claim 13, having a diameter of from about 15 mm to about 27 mm.

* * * * *